United States Patent
Okuyama et al.

(10) Patent No.: US 10,059,679 B2
(45) Date of Patent: Aug. 28, 2018

(54) METHOD FOR PRODUCING POLYMERIZABLE COMPOUND

(71) Applicant: ZEON CORPORATION, Chiyoda-ku, Tokyo (JP)

(72) Inventors: Kumi Okuyama, Tokyo (JP); Kanako Sanuki, Tokyo (JP); Kei Sakamoto, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 95 days.

(21) Appl. No.: 15/124,092

(22) PCT Filed: Mar. 19, 2015

(86) PCT No.: PCT/JP2015/058266
§ 371 (c)(1),
(2) Date: Sep. 7, 2016

(87) PCT Pub. No.: WO2015/141784
PCT Pub. Date: Sep. 24, 2015

(65) Prior Publication Data
US 2017/0015639 A1 Jan. 19, 2017
US 2017/0190679 A9 Jul. 6, 2017

(30) Foreign Application Priority Data

Mar. 19, 2014 (JP) .................. 2014-057042

(51) Int. Cl.
*C07D 277/82* (2006.01)
*C08F 22/26* (2006.01)
(Continued)

(52) U.S. Cl.
CPC ............ *C07D 277/82* (2013.01); *C07C 67/14* (2013.01); *C07C 69/75* (2013.01); *C07C 69/757* (2013.01); *C08F 22/26* (2013.01); *C07C 2601/14* (2017.05)

(58) Field of Classification Search
CPC ....... C07D 277/82; C07C 67/14; C07C 69/75; C07C 69/757; C08F 22/26
See application file for complete search history.

(56) References Cited

U.S. PATENT DOCUMENTS 5,567,349 A 10/1996 Kelly et al.
6,139,771 A 10/2000 Walba et al.
(Continued)

FOREIGN PATENT DOCUMENTS

CN 101470212 A 7/2009
EP 2871192 A1 5/2015
(Continued)

OTHER PUBLICATIONS

Sep. 20, 2016, International Preliminary Report on Patentability issued in the International Patent Application No. PCT/JP2015/058266.
(Continued)

*Primary Examiner* — Joseph R Kosack
(74) *Attorney, Agent, or Firm* — Kenja IP Law PC

(57) ABSTRACT

Provided is a method for producing a polymerizable compound represented by a formula (I) comprising:
a step (1) that reacts a compound represented by a formula (II) with 2,5-dihydroxybenzaldehyde in an organic solvent in the presence of a base to obtain a reaction mixture including a compound represented by a formula (III); and
a step (2) that adds a compound represented by a formula (IV) and an acidic aqueous solution to the reaction mixture obtained by the step (1) to effect a reaction, wherein A represents a hydrogen atom, a methyl group or the like, L represents a leaving group, n represents an integer from 1 to 20, X represents an oxygen atom, a sulfur atom, $-C(R^1)(R^2)-$ or the like, R represents a hydrogen atom, an organic group or the like, and each of $R^x$ represents a hydrogen atom, a halogen atom or the like. According to the present invention, provided is a method for producing a polymerizable compound represented by a formula (I) at high purity and at high yield.

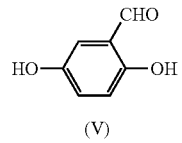

(V)

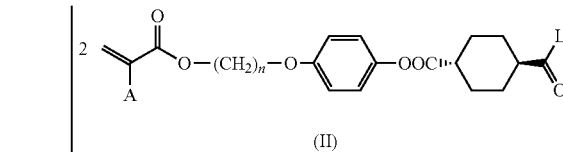

(II)

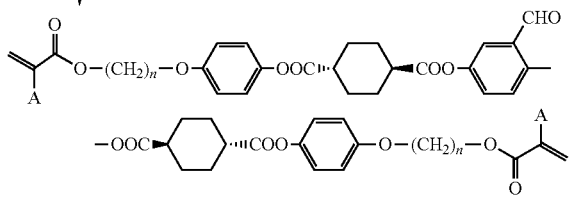

(III)

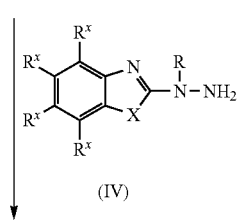

(IV)

(Continued)

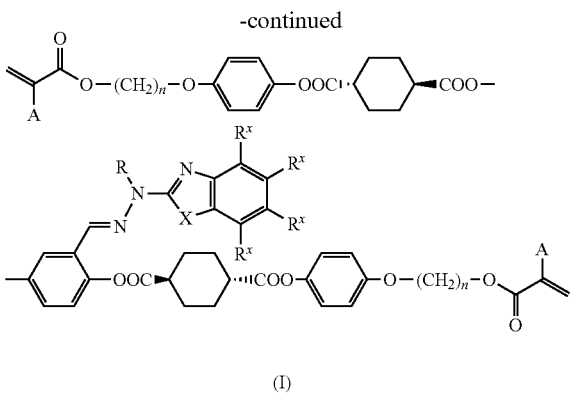

(I)

6 Claims, No Drawings

(51) Int. Cl.
  C07C 69/757 (2006.01)
  C07C 69/75 (2006.01)
  C07C 67/14 (2006.01)

(56) References Cited

U.S. PATENT DOCUMENTS

| 6,203,724 | B1 | 3/2001 | Reiffenrath et al. |
| 6,565,974 | B1 | 5/2003 | Uchiyama et al. |
| 2002/0159005 | A1 | 10/2002 | Arakawa et al. |
| 2003/0102458 | A1 | 6/2003 | Nishikawa et al. |
| 2007/0176145 | A1 | 8/2007 | Nishikawa et al. |
| 2007/0298191 | A1 | 12/2007 | Yamahara et al. |
| 2009/0072194 | A1 | 3/2009 | Yamahara et al. |
| 2009/0189120 | A1 | 7/2009 | Takeuchi |
| 2010/0201920 | A1 | 8/2010 | Adlem et al. |
| 2010/0301271 | A1 | 12/2010 | Adlem et al. |
| 2015/0175564 | A1 | 6/2015 | Sakamoto et al. |
| 2015/0277010 | A1 | 10/2015 | Aimatsu et al. |
| 2016/0200841 | A1 | 7/2016 | Sakamoto |
| 2016/0257659 | A1 | 9/2016 | Sakamoto et al. |

FOREIGN PATENT DOCUMENTS

| JP | H1068816 A | 3/1998 |
| JP | H1090521 A | 4/1998 |
| JP | H1152131 A | 2/1999 |
| JP | 2000284126 A | 10/2000 |
| JP | 2001004837 A | 1/2001 |
| JP | 2002267838 A | 9/2002 |
| JP | 2003160540 A | 6/2003 |
| JP | 2005208414 A | 8/2005 |
| JP | 2005208415 A | 8/2005 |
| JP | 2005208416 A | 8/2005 |
| JP | 2005289980 A | 10/2005 |
| JP | 2006330710 A | 12/2006 |
| JP | 2009179563 A | 8/2009 |
| JP | 2010031223 A | 2/2010 |
| JP | 2010537954 A | 12/2010 |
| JP | 2010537955 A | 12/2010 |
| JP | 2011006360 A | 1/2011 |
| JP | 2011006361 A | 1/2011 |
| JP | 2011042606 A | 3/2011 |
| WO | 0026705 A1 | 5/2000 |
| WO | 2006052001 A1 | 5/2006 |
| WO | 2014010325 A1 | 1/2014 |
| WO | 2014065243 A1 | 5/2014 |
| WO | 2015025793 A1 | 2/2015 |
| WO | 2015064698 A1 | 5/2015 |

OTHER PUBLICATIONS

Oct. 9, 2017, Extended European Search Report issued by the European Patent Office in the corresponding European Patent Application No. 15764820.5.

Jun. 30, 2015, International Search Report issued in the International Patent Application No. PCT/JP2015/058266.

METHOD FOR PRODUCING POLYMERIZABLE COMPOUND

TECHNICAL FIELD

The present invention relates to a method by which a polymerizable compound that can produce an optical film that achieves uniform conversion of polarized light over a wide wavelength band, can be produced in high purity and high yield.

BACKGROUND ART

A quarter-wave plate that converts linearly polarized light into circularly polarized light, a half-wave plate that changes (converts) the plane of vibration of linearly polarized light by 90°, and the like are known as a retardation film that is used for a flat panel display (FPD) and the like. These retardation films can achieve accurate conversion of specific monochromatic light so that ¼λ or ½λ retardation occurs. In recent years, various wideband retardation films that can achieve uniform retardation with respect to light over a wide wavelength band (i.e., retardation films having reverse wavelength dispersion) have been studied (see Patent Literature 1 to 6, for example).

It has been desired to reduce the thickness of the flat panel display as much as possible along with an improvement in functionality and widespread use of mobile information terminals (e.g., mobile personal computer and mobile phone). Therefore, a reduction in thickness of the retardation film has also been desired.

It has been considered that the thickness of the retardation film can be effectively reduced by producing the retardation film by applying a polymerizable composition that includes a low-molecular-weight polymerizable compound to a film substrate. Various low-molecular-weight polymerizable compounds having excellent wavelength dispersion, and various polymerizable compositions using such polymerizable compounds have been developed (see Patent Literature 7 to 24, for example).

However, the low-molecular-weight polymerizable compounds or the polymerizable compositions disclosed in Patent Literature 7 to 24 have a number of problems in that the reverse wavelength dispersion may be insufficient, or it may be difficult to apply the low-molecular-weight polymerizable compounds or the polymerizable compositions to a film due to a high melting point that is not suitable for an industrial process, or the temperature range in which the liquid crystallinity is obtained may be very narrow, or the solubility in a solvent commonly used for an industrial process may be low. Moreover, since these low-molecular-weight polymerizable compounds and the like are synthesized through a plurality of steps using a synthesis method that utilizes an expensive reagent, an increase in production cost occurs.

Since an optical defect occurs when ionic impurities (e.g., halogen or alkali) are included in a compound used to produce an optical member, it has been desired to reduce the ionic impurity content when producing a polymerizable compound.

CITATION LIST

Patent Literature

Patent Literature 1: JP-A-10-68816
Patent Literature 2: JP-A-10-90521
Patent Literature 3: JP-A-11-52131
Patent Literature 4: JP-A-2000-284126 (US20020159005A1)
Patent Literature 5: JP-A-2001-4837
Patent Literature 6: WO2000/026705
Patent Literature 7: JP-A-2002-267838
Patent Literature 8: JP-A-2003-160540 (US20030102458A1)
Patent Literature 9: JP-A-2005-208414
Patent Literature 10: JP-A-2005-208415
Patent Literature 11: JP-A-2005-208416
Patent Literature 12: JP-A-2005-289980 (US20070176145A1)
Patent Literature 13: JP-A-2006-330710 (US20090072194A1)
Patent Literature 14: JP-A-2009-179563 (US20090189120A1)
Patent Literature 15: JP-A-2010-31223
Patent Literature 16: JP-A-2011-6360
Patent Literature 17: JP-A-2011-6361
Patent Literature 18: JP-A-2011-42606
Patent Literature 19: JP-T-2010-537954 (US20100201920A1)
Patent Literature 20: JP-T-2010-537955 (US20100301271A1)
Patent Literature 21: WO2006/052001 (US20070298191A1)
Patent Literature 22: U.S. Pat. No. 6,139,771
Patent Literature 23: U.S. Pat. No. 6,203,724
Patent Literature 24: U.S. Pat. No. 5,567,349

SUMMARY OF INVENTION

Technical Problem

The applicant of the present application reported that a polymerizable compound represented by the following formula has a practical low melting point, exhibits excellent solubility in a general-purpose solvent, can be produced at low cost, and can produce an optical film that can achieve uniform conversion of polarized light over a wide wavelength band (see WO2014/010325).

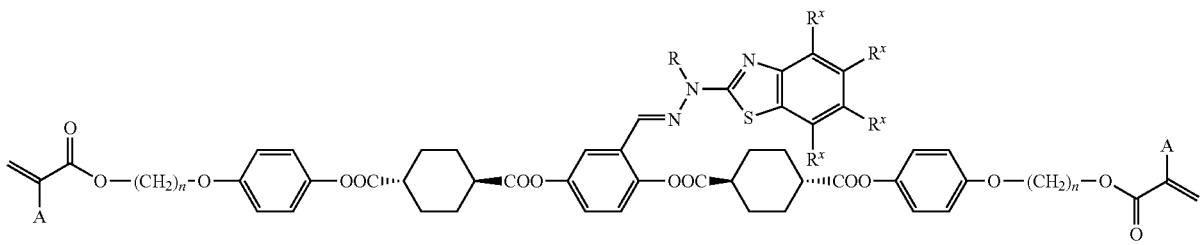

wherein A represents a hydrogen atom, a methyl group, or a chlorine atom, R represents a hydrogen atom, or an organic group having 1 to 20 carbon atoms, $R^x$ represents a hydrogen atom, a halogen atom, or the like, and n represents an integer from 1 to 20.

An object of the invention is to provide a method that can industrially advantageously produce the polymerizable compound represented by the above formula (formula (I)) in high purity and high yield.

Solution to Problem

The inventors of the invention conducted extensive studies in order to solve the above problem. As a result, the inventors found that a high-purity polymerizable compound represented by the following formula (I) that has a very low ionic impurity content can be obtained in high yield by reacting a compound represented by the following formula (II) with 2,5-dihydroxybenzaldehyde in an organic solvent in the presence of a base to obtain a reaction mixture including a compound represented by the following formula (III), and adding a compound represented by the following formula (IV) and an acidic aqueous solution to the reaction mixture to effect a reaction in a state in which a salt produced by the above reaction is completely dissolved in the acidic aqueous solution. This finding has led to the completion of the invention.

One aspect of the invention provides the following method for producing a polymerizable compound (see (1) to (5)).

(1) A method for producing a polymerizable compound represented by the following formula (I) including a step (1) that reacts a compound represented by the following formula (II) with 2,5-dihydroxybenzaldehyde in an organic solvent in the presence of a base to obtain a reaction mixture including a compound represented by the following formula (III), and a step (2) that adds a compound represented by the following formula (IV) and an acidic aqueous solution to the reaction mixture obtained by the step (1) to effect a reaction,

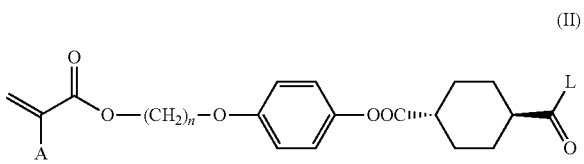

wherein A represents a hydrogen atom, a methyl group, or a chlorine atom, L represents a leaving group, and n represents an integer from 1 to 20,

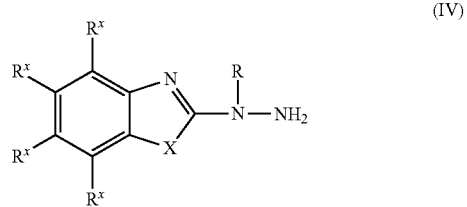

wherein A and n are the same as defined above, wherein X represents an oxygen atom, a sulfur atom, —C($R^1$)($R^2$)—, or —N—$R^1$—, wherein each of $R^1$ and $R^2$ independently represents a hydrogen atom, or a substituted or unsubstituted alkyl group having 1 to 10 carbon atoms, R represents a hydrogen atom, or a substituted or unsubstituted organic group having 1 to 20 carbon atoms, and each of $R^x$ represents a hydrogen atom, a halogen atom, an alkyl group having 1 to 6 carbon atoms, a cyano group, a nitro group, a fluoroalkyl group having 1 to 6 carbon atoms, an alkoxy group having 1 to 6 carbon atoms, an alkylthio group having 1 to 6 carbon atoms, a monosubstituted amino group, a disubstituted amino group, or —C(=O)—O—$R^3$, wherein $R^3$ is the same as defined above in connection with $R^1$ and $R^2$, provided that $R^x$ are identical to or different from each other, and an arbitrary C—$R^x$ that forms the ring is optionally substituted with a nitrogen atom,

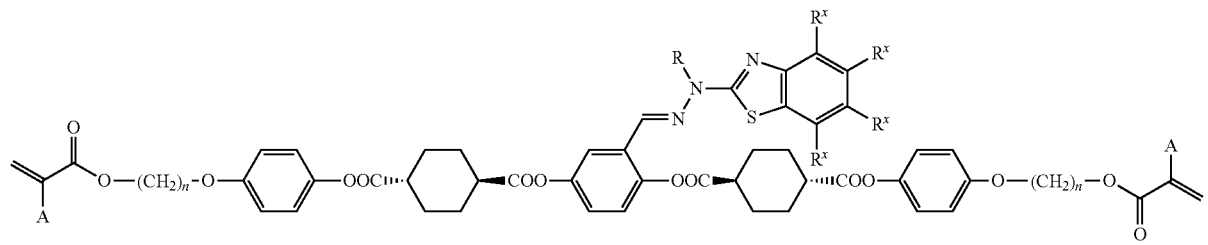

(I)

wherein A, R, $R^x$, X, and n are the same as defined above.

(2) The method according to (1), wherein R included in the compound represented by the formula (IV) is a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted aromatic group having 6 to 18 carbon atoms, or a substituted or unsubstituted heteroaromatic group having 4 to 18 carbon atoms.

(3) The method according to (1) or (2), wherein each of $R^x$ included in the compound represented by the formula (IV) is a hydrogen atom.

(4) The method according to any one of (1) to (3), wherein the acid component included in the acidic aqueous solution is an inorganic acid or an organic acid having 1 to 20 carbon atoms.

(5) The method according to any one of (1) to (4), wherein the acid component included in the acidic aqueous solution is at least one acid selected from the group consisting of hydrochloric acid, sulfuric acid, phosphoric acid, boric acid, a sulfonic acid, a sulfinic acid, formic acid, acetic acid, and oxalic acid.

Advantageous Effects of Invention

The polymerizable compound represented by the formula (I) that has a practical low melting point, exhibits excellent solubility in a general-purpose solvent, can be produced at low cost, and can produce an optical film that can achieve uniform conversion of polarized light over a wide wavelength band, can be produced in high purity and high yield by utilizing the method according to one aspect of the invention.

Since the method according to one aspect of the invention effects the reactions in a continuous manner, the method according to one aspect of the invention is simple in terms of operation, and is highly economical.

DESCRIPTION OF EMBODIMENTS

The exemplary embodiments of the invention are described in detail below.

Note that the expression "substituted or unsubstituted" used herein in connection with a group or the like means that the group or the like is unsubstituted, or substituted with a substituent.

According to one embodiment of the invention, a method for producing a polymerizable compound represented by the following formula (I) (hereinafter may be referred to as "polymerizable compound (I)") includes a step (1) that reacts a compound represented by the following formula (II) (hereinafter may be referred to as "compound (II)") with 2,5-dihydroxybenzaldehyde represented by the following formula (V) (hereinafter may be referred to as "compound (V)") in an organic solvent in the presence of a base to obtain a reaction mixture including a compound represented by the following formula (III) (hereinafter may be referred to as "compound (III)"), and a step (2) that adds a compound represented by the following formula (IV) (hereinafter may be referred to as "compound (IV)") and an acidic aqueous solution to the reaction mixture obtained by the step (1) to effect a reaction.

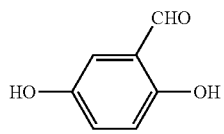

(V)

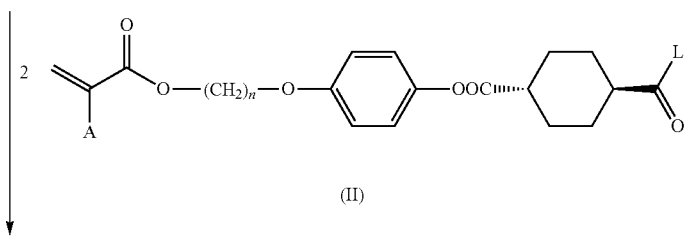

(II)

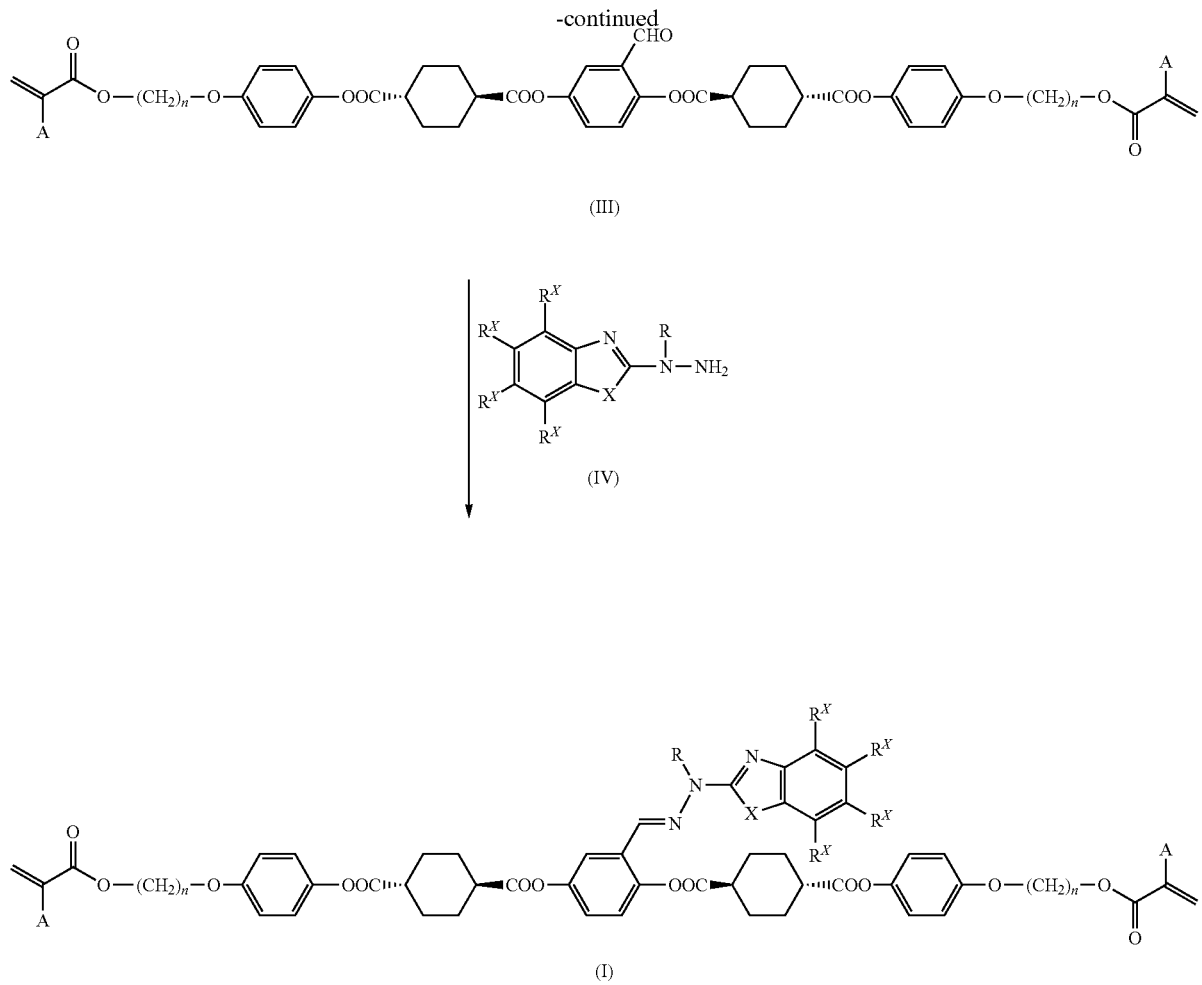

Step (1)

In the step (1), the compound (II) is reacted with the compound (V) in an organic solvent in the presence of a base to obtain a reaction mixture including the compound (III).

A included in the compound (II) represented by the formula (II) represents a hydrogen atom, a methyl group, or a chlorine atom, and is preferably a hydrogen atom.

L represents a leaving group. Examples of the leaving group include a hydroxyl group; a halogen atom such as a chlorine atom, a bromine atom, and an iodine atom; an organic sulfonyloxy group such as a methanesulfonyloxy group, a p-toluenesulfonyloxy group, a trifluoromethylsulfonyloxy group, and a camphorsulfonyloxy group; and the like. Among these, a halogen atom is preferable, and a chlorine atom is more preferable, since the target product can be obtained at low cost in high yield.

n represents an integer from 1 to 20. n is preferably an integer from 2 to 8, and more preferably 6.

The compound (V) and the compound (II) are used in a molar ratio (compound (V):compound (II)) of 1:2 to 1:4, and preferably 1:2 to 1:3.

Note that a compound (III-1) that includes different groups on the right side and the left side can be obtained by effecting a stepwise reaction using two different compounds (II) (compound (II-1) and compound (II-2)) (see below). Specifically, 1 mol of the compound (II-1) is reacted with 1 mol of the compound (V), and 1 mol of the compound (II-2) is reacted with the resulting product to obtain the compound (III-1). Note that L in the following formulas is the same as defined above. $A_1$ and $A_2$ are the same as defined above in connection with A, and n1 and n2 are the same as defined above in connection with n, provided that $A_1$ and $A_2$ or n1 and n2 differ from each other. L in the formula (II-1) and L in the formula (II-2) are either identical to or different from each other.

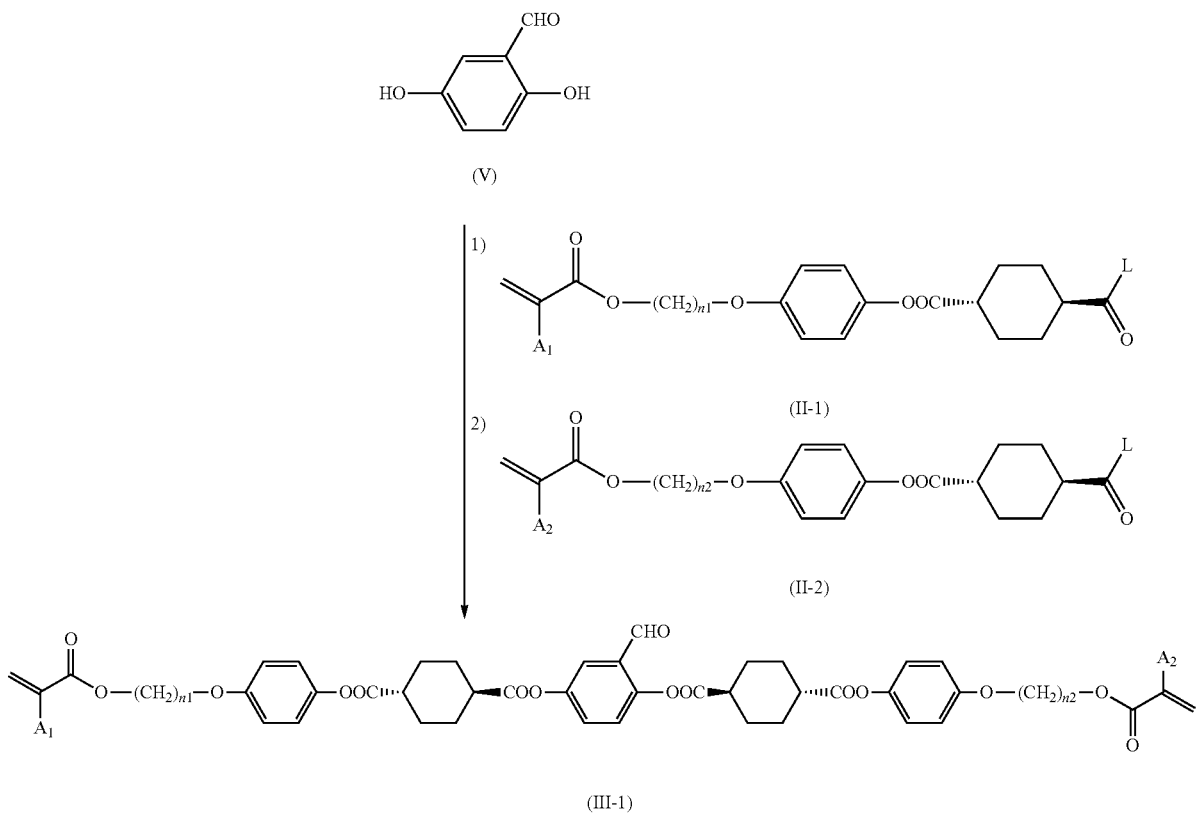

Examples of the base used in the step (1) include an organic base such as triethylamine, diisopropylethylamine, pyridine, and 4-(dimethylamino)pyridine; and an inorganic base such as sodium hydroxide, sodium carbonate, and sodium hydrogen carbonate.

The base is normally used in a ratio of 1 to 3 mol based on 1 mol of the compound (II).

When L included in the compound represented by the formula (II) is a hydroxyl group, the reaction may be effected in the presence of a dehydration-condensation agent such as N,N-dicyclohexylcarbodiimide or 1-ethyl-3-(3-dimethylaminopropyl)carbodiimide hydrochloride.

The reaction is effected in an organic solvent. The organic solvent is not particularly limited as long as the organic solvent is inert to the reaction. Examples of the organic solvent include a chlorine-based solvent such as chloroform and methylene chloride; an amide-based solvent such as N-methylpyrrolidone, N,N-dimethylformamide, N,N-dimethylacetamide, and hexamethylphosphoric triamide; an ether-based solvent such as 1,4-dioxane, cyclopentyl methyl ether, tetrahydrofuran, tetrahydropyran, and 1,3-dioxolane; a sulfur-containing solvent such as dimethyl sulfoxide and sulfolane; a nitrile-based solvent such as acetonitrile; an ester-based solvent such as ethyl acetate and propyl acetate; an aromatic hydrocarbon-based solvent such as benzene, toluene, and xylene; an aliphatic hydrocarbon-based solvent such as n-pentane, n-hexane, and n-octane; an alicyclic hydrocarbon-based solvent such as cyclopentane and cyclohexane; a mixed solvent including two or more solvents among these solvents; and the like.

Among these, a polar solvent such as an amide-based solvent and an ether-based solvent is preferable since the target product can be obtained in high yield.

The organic solvent may be used in an appropriate amount taking account of the type of each compound, the reaction scale, and the like. The organic solvent is normally used in an amount of 1 to 50 g per gram of the compound (II).

Examples of the reaction method include (a) a method that adds the compound (II) or an organic solvent solution including the compound (II) to an organic solvent solution including the compound (V) and the base, (β) a method that adds the compound (V) or an organic solvent solution including the compound (V) to an organic solvent solution including the compound (II) and the base, (γ) a method that adds the base to an organic solvent solution including the compound (V) or the compound (II), and the like. It is preferable to use the method (α) since the target product can be obtained in high yield.

The reaction temperature is set to a temperature within a range from $-20°$ C. to the boiling point of the solvent, and preferably $-15$ to $+30°$ C.

The reaction time is determined taking account of the reaction scale, but is normally set to several minutes to several hours.

The resulting reaction mixture is subjected directly to the step (2) without washing, extraction, and the like while being maintained at the above temperature.

Note that the compound (V) and many of the compounds (II) are known compounds, and may be produced using a known method (e.g., the method disclosed in WO2014/010325). A commercially-available product may be used as the compound (V) either directly or after purification.

For example, the compound (II) wherein L is a halogen atom (hal) may be produced as described below (see the following reaction formula).

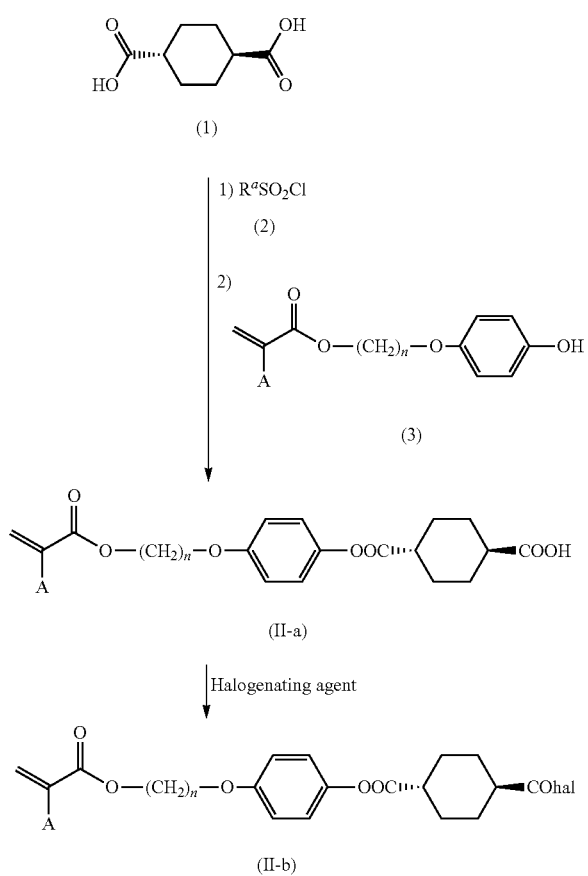

wherein A and n are the same as defined above, IV represents an alkyl group (e.g., methyl group or ethyl group), or a substituted or unsubstituted aryl group (e.g., phenyl group, p-methylphenyl group, or 10-(7,7-dimethyl-2-oxobicyclo [2.2.1]heptyl) group), and hal represents a halogen atom (e.g., chlorine atom or bromine atom).

Specifically, the sulfonyl chloride represented by the formula (2) is reacted with trans-1,4-cyclohexanedicarboxylic acid (compound (1)) represented by the formula (1) in the presence of a base (e.g., triethylamine or 4-(dimethylamino)pyridine).

The compound (3) and a base (e.g., triethylamine or 4-(dimethylamino)pyridine) are added to the reaction mixture to effect a reaction to obtain the compound represented by the formula (II-a).

The sulfonyl chloride is normally used in a ratio of 0.5 to 1.0 equivalent based on 1 equivalent of the compound (1).

The compound (3) is normally used in a ratio of 0.5 to 1.0 equivalent based on 1 equivalent of the compound (1).

The base is normally used in a ratio of 1.0 to 2.5 equivalents based on 1 equivalent of the compound (1).

The reaction temperature is set to 20 to 30° C. The reaction time is determined taking account of the reaction scale and the like, but is normally set to several minutes to several hours.

A halogenating agent (e.g., thionyl chloride, thionyl bromide, or sulfuryl chloride) is then reacted with the compound represented by the formula (II-a) to obtain the compound represented by the formula (II-b).

Examples of a solvent used for the reaction for obtaining the compound represented by the formula (II-a) include those mentioned above in connection with the solvent that may be used when producing the compound (III). It is preferable to use an ether-based solvent.

Examples of a solvent used for the reaction for obtaining the compound represented by the formula (II-b) include an amide-based solvent such as N,N-dimethylformamide and N,N-dimethylacetamide; an aromatic hydrocarbon-based solvent such as benzene and toluene; a mixed solvent including two or more solvents among these solvents; and the like.

The solvent may be used in an appropriate amount taking account of the type of each compound, the reaction scale, and the like. The solvent is normally used in an amount of 1 to 50 g per gram of the compound (1).

Step (2)

In the step (2), the compound (IV) and the acidic aqueous solution are added to the reaction mixture obtained by the step (1) to react the compound (III) and the compound (IV).

The target polymerizable compound (I) can be obtained in high yield and high purity through this reaction.

X included in the compound (IV) (represented by the formula (IV)) represents an oxygen atom, a sulfur atom, —C($R^1$)($R^2$)—, or —N—$R^1$—. Note that each of $R^1$ and $R^2$ independently represents a hydrogen atom, or a substituted or unsubstituted alkyl group having 1 to 10 carbon atoms.

Examples of the alkyl group having 1 to 10 carbon atoms that forms the substituted or unsubstituted alkyl group having 1 to 10 carbon atoms represented by $R^1$ and $R^2$ include a methyl group, an ethyl group, an n-propyl group, an isopropyl group, an n-butyl group, a sec-butyl group, a t-butyl group, an n-pentyl group, an isopentyl group, a neopentyl group, an n-hexyl group, an isohexyl group, a 3-heptyl group, an n-octyl group, an n-nonyl group, an n-decyl group, and the like.

Examples of a substituent that may substitute the alkyl group having 1 to 10 carbon atoms include a halogen atom such as a fluorine atom and a chlorine atom; a cyano group; a substituted amino group such as a dimethylamino group; an alkoxy group having 1 to 6 carbon atoms, such as a methoxy group and an ethoxy group; a nitro group; an aryl group such as a phenyl group; a cycloalkyl group having 3 to 8 carbon atoms, such as a cyclopropyl group and a cyclopentyl group; a hydroxyl group; and the like.

It is preferable that X be an oxygen atom, a sulfur atom, or —CH$_2$—, more preferably an oxygen atom or a sulfur atom, and particularly preferably a sulfur atom, since the advantageous effects of the invention can be more easily achieved.

R represents a substituted or unsubstituted organic group having 1 to 20 carbon atoms. Examples of the organic group having 1 to 20 carbon atoms include a hydrocarbon group such as an alkyl group having 1 to 20 carbon atoms, a cycloalkyl group having 3 to 20 carbon atoms, an alkenyl group having 2 to 20 carbon atoms, an alkynyl group having 2 to 20 carbon atoms, and an aromatic group having 6 to 20 carbon atoms; a heteroaromatic group; a carboxyl group; an acid anhydride group; an amide group; and the like.

Examples of the alkyl group having 1 to 20 carbon atoms include a methyl group, an ethyl group, an n-propyl group, an isopropyl group, an n-butyl group, a sec-butyl group, a t-butyl group, an n-pentyl group, an n-hexyl group, an n-heptyl group, an n-undecyl group, an n-dodecyl group, a 1-methylpentyl group, a 1-ethylpentyl group, and the like.

Examples of the cycloalkyl group having 3 to 20 carbon atoms include a cyclopropyl group, a cyclobutyl group, a cyclopentyl group, a cyclohexyl group, and the like.

Examples of the alkenyl group having 2 to 20 carbon atoms include a vinyl group, an allyl group, an isopropenyl group, a butenyl group, and the like.

Examples of the alkynyl group having 2 to 20 carbon atoms include a propynyl group, a butynyl group, and the like.

Examples of the aromatic group having 6 to 20 carbon atoms include a phenyl group, a 1-naphthyl group, a 2-naphthyl group, and the like.

Examples of the heteroaromatic group include a thienyl group, a pyrrolyl group, a furyl group, a pyridyl group, a piperidyl group, a quinolyl group, an isoquinolyl group, a pyrimidyl group, and a triazinyl group.

Examples of a substituent that may substitute the alkyl group, the alkenyl group, and the alkynyl group include a halogen atom such as a fluorine atom and a chlorine atom; a cyano group; a hydroxyl group; a substituted amino group such as a dimethylamino group; an alkoxy group having 1 to 6 carbon atoms, such as a methoxy group, an ethoxy group, an isopropoxy group, and an n-butoxy group; an alkoxy group having 1 to 6 carbon atoms that is substituted with an alkoxy group having 1 to 6 carbon atoms, such as a methoxymethoxy group and a methoxyethoxy group; a cycloalkyl group having 3 to 8 carbon atoms, such as a cyclopropyl group, a cyclopentyl group, a cyclohexyl group, and a cycloheptyl group; a nitro group; an aryl group such as a phenyl group, a 4-chlorophenyl group, and a naphthyl group; a —C(=O)—OR$^b$ group; an —SO$_2$R$^b$ group; and the like. Note that R$^b$ represents an alkyl group having 1 to 6 carbon atoms, or an aryl group having 6 to 14 carbon atoms.

Examples of a substituent that may substitute the cycloalkyl group, the aromatic group, and the heteroaromatic group include a halogen atom such as a fluorine atom and a chlorine atom; a cyano group; a hydroxyl group; an alkyl group having 1 to 6 carbon atoms, such as a methyl group, an ethyl group, a propyl group, and an n-butyl group; an alkenyl group having 2 to 6 carbon atoms, such as a vinyl group and an allyl group; an alkyl halide group having 1 to 6 carbon atoms, such as a trifluoromethyl group; a substituted amino group such as a dimethylamino group; an alkoxy group having 1 to 6 carbon atoms, such as a methoxy group, an ethoxy group, and an isopropoxy group; an alkoxy group having 1 to 6 carbon atoms that is substituted with an alkoxy group having 1 to 6 carbon atoms, such as a methoxymethoxy group and a methoxyethoxy group; a cycloalkyl group having 3 to 8 carbon atoms, such as a cyclopropyl group, a cyclopentyl group, a cyclohexyl group, and a cycloheptyl group; a nitro group; an aryl group such as a phenyl group, a 4-chlorophenyl group, and a naphthyl group; a —C(=O)—OR$^b$ group; an —SO$_2$R$^b$ group; and the like. Note that R$^b$ is the same as defined above.

It is preferable that R be a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted aromatic group having 6 to 18 carbon atoms, or a substituted or unsubstituted heteroaromatic group having 4 to 18 carbon atoms, and particularly preferably a substituted or unsubstituted alkyl group having 1 to 20 carbon atoms.

Each of R$^X$ represents a hydrogen atom, a halogen atom (e.g., fluorine atom, chlorine atom, or a bromine atom), an alkyl group having 1 to 6 carbon atoms (e.g., methyl group or ethyl group), a cyano group, a nitro group, a fluoroalkyl group having 1 to 6 carbon atoms (e.g., trifluoromethyl group or pentafluoroethyl group), an alkoxy group having 1 to 6 carbon atoms (e.g., methoxy group or ethoxy group), an alkylthio group having 1 to 6 carbon atoms (e.g., methylthio group or ethylthio group), a monosubstituted amino group (e.g., methylamino group or ethylamino group), a disubstituted amino group (e.g., dimethylamino group or diethylamino group), or —C(=O)—O—R$^3$. Note that R$^3$ represents a hydrogen atom, or a substituted or unsubstituted alkyl group having 1 to 10 carbon atoms.

Examples of the substituted or unsubstituted alkyl group having 1 to 10 carbon atoms represented by R$^3$ include those mentioned above in connection with the substituted or unsubstituted alkyl group having 1 to 10 carbon atoms that may be represented by R$^1$ and the like.

It is preferable that R$^X$ be a hydrogen atom.

R$^X$ are identical to or different from each other, and an arbitrary C—R$^X$ that forms the ring is optionally substituted with a nitrogen atom. Specific examples of the compound (IV) in which one or more C—R$^X$ are substituted with a nitrogen atom include, but are not limited to, the compounds shown below.

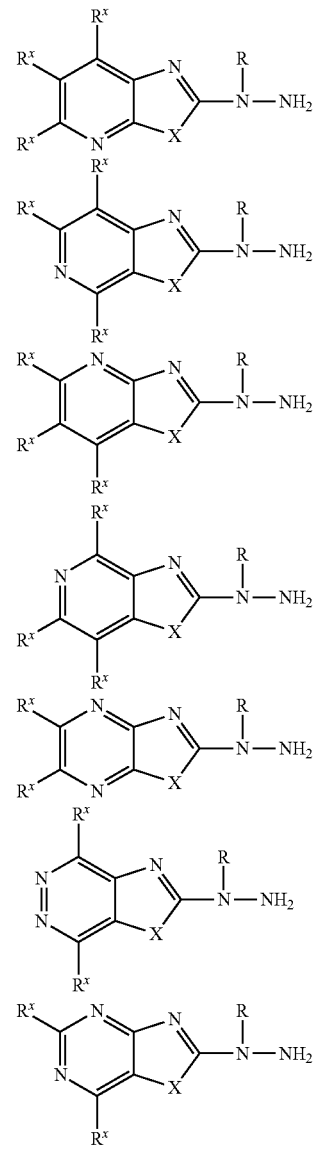

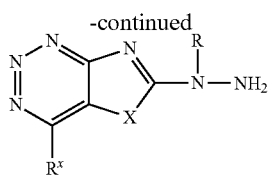

wherein R, X, and $R^X$ are the same as defined above (hereinafter the same).

The compound (IV) is used in such an amount that the molar ratio (compound (III):compound (IV)) of the compound (III) to the compound (IV) is 1:1 to 1:2, and preferably 1:1 to 1:1.5.

The acidic aqueous solution is not particularly limited. It is preferable that the acidic aqueous solution have a pH of 6 or less, and more preferably 2 or less.

Examples of the acid component included in the acidic aqueous solution include an inorganic acid such as hydrochloric acid, sulfuric acid, phosphoric acid, carbonic acid, boric acid, perchloric acid, and nitric acid; and an organic acid such as a carboxylic acid such as formic acid, acetic acid, oxalic acid, citric acid, and trifluoroacetic acid; a sulfonic acid such as p-toluenesulfonic acid, methanesulfonic acid, trifluoromethanesulfonic acid, and 10-camphorsulfonic acid; and a sulfinic acid such as benzenesulfinic acid. These acid components may be used either alone or in combination.

Among these, an inorganic acid and an organic acid having 1 to 20 carbon atoms are preferable, hydrochloric acid, sulfuric acid, phosphoric acid, boric acid, a sulfonic acid, a sulfinic acid, formic acid, acetic acid, and oxalic acid are more preferable, and hydrochloric acid and a sulfonic acid are particularly preferable, since the target product can be obtained in high yield.

The concentration of the acidic aqueous solution is preferably 0.1 to 2 mol/L.

The acidic aqueous solution is preferably used in such an amount that, when the compound (IV) and the acidic aqueous solution are added to the reaction mixture, a reaction can be effected in a state in which a salt produced by the above reaction is completely dissolved in the acidic aqueous solution. For example, when a 1.0 N acidic aqueous solution is used, the acidic aqueous solution is used in a ratio of 1 to 20 parts by mass, and preferably 5 to 15 parts by mass, based on 10 parts by mass of the compound (II).

In the step (2), the reaction is effected in a state in which the compound (IV) and the acidic aqueous solution are added to the reaction mixture obtained by the step (1). Since the reaction mixture obtained by the step (1) is used directly without a post-treatment operation (e.g., washing and extraction) (see above), it is possible to reduce cost.

The compound (IV) may optionally be added after dissolving the compound (IV) in an appropriate organic solvent. Examples of the organic solvent include those mentioned above in connection with the step (1).

The method according to the embodiments of the invention is characterized in that the high-purity polymerizable compound (I) having a very low ionic impurity content can be obtained in high yield since the compound (IV) and the acidic aqueous solution are added to the reaction mixture obtained by the step (1) to effect a reaction in a state in which a salt produced by the reaction is completely dissolved in the acidic aqueous solution. It is considered that, when the acidic aqueous solution is added to the reaction mixture including the compound (III), a salt included in the reaction mixture that has been produced as a by-product through the reaction effected in the step (1) is completely dissolved in the acidic aqueous solution and excluded from the reaction system, and the ionic impurity content in the polymerizable compound (I) obtained by the reaction between the compound (III) and the compound (IV) decreases, so that the target product can be obtained in high purity.

When implementing the method according to the embodiments of the invention, it is preferable that at least one of the organic solvent (first organic solvent) used in the step (1), and the organic solvent (second organic solvent) used in the step (2) when adding the compound (IV) in the form of a solution in an organic solvent, be a water-immiscible organic solvent. When the water-immiscible organic solvent is used as either or both of the first organic solvent and the second organic solvent, it is possible to obtain the polymerizable compound (I) that has a lower ionic impurity content (i.e., has higher purity) in higher yield.

The term "water-immiscible organic solvent" used herein refers to an organic solvent that has a solubility in water (20° C.) of 10 g (organic solvent)/100 mL (water) or less, preferably 1 g (organic solvent)/100 mL (water) or less, and more preferably 0.1 g (organic solvent)/100 mL (water) or less.

Examples of the water-immiscible organic solvent include an ester such as ethyl acetate, isopropyl acetate, butyl acetate, dimethyl carbonate, and diethyl carbonate; a halogenated hydrocarbon such as methylene chloride, chloroform, and 1,2-dichloroethane; an aromatic hydrocarbon such as benzene, toluene, and xylene; a saturated hydrocarbon such as pentane, hexane, and heptane; an ether such as diethyl ether and cyclopentyl methyl ether; an alicyclic hydrocarbon such as cyclopentane and cyclohexane; and the like.

The reaction temperature during the step (2) is set to a temperature within a range from −20° C. to the boiling point of the solvent, and preferably 0 to 80° C. The reaction time is determined taking account of the reaction scale, but is normally set to several minutes to 10 hours.

When the reaction mixture is separated into an organic layer and an aqueous layer, water (sodium chloride solution) and a water-immiscible organic solvent are optionally added to the reaction mixture to effect separation, and the organic layer is collected.

When the reaction mixture is not separated into two layers, water (sodium chloride solution) and a water-immiscible organic solvent are optionally added to the reaction mixture to effect separation, and the organic layer is collected.

In either case, the organic layer is subjected to a post-treatment operation that is normally employed in synthetic organic chemistry, optionally followed by a known separation-purification means (e.g., precipitation, recrystallization, distillation, and column chromatography) to isolate the target compound (I).

Either or both of an adsorbent and a filter aid may be used to reduce the ionic impurity content and remove an insoluble substance (high-molecular-weight substance).

Examples of the adsorbent include activated carbon, silica gel (main component: $SiO_2$), a synthetic adsorbent (main component: MgO, $Al_2O_3$, and $SiO_2$), activated clay, alumina, an ion-exchange resin, an adsorbent resin, and the like.

Examples of the filter aid include diatomaceous earth, silica gel (main component: $SiO_2$), a synthetic zeolite, pearlite, Radiolite, and the like.

When implementing the method according to the embodiments of the invention, it is preferable to use a method that concentrates the resulting organic layer, and precipitates crystals of the target product from the concentrate, or a method that concentrates the resulting organic layer, and adds a poor solvent to the concentrate to precipitate crystals of the target product, since the high-purity target product can be obtained in high yield using a simple operation.

Examples of the poor solvent used for the latter method include water; an alcohol such as methanol and ethanol; and the like.

It is also preferable to purify the resulting crystals using a recrystallization method.

The term "recrystallization method" used herein refers to a method that dissolves the resulting (crude) crystals in a small amount of solvent (so that part of the crystals remains undissolved), heats the solution to effect complete dissolution, subjects the resulting solution to hot filtration to remove an insoluble substance, and cools the filtrate to precipitate crystals.

Examples of the solvent used for recrystallization include those mentioned above in connection with the poor solvent used for the precipitation method, and an ether such as tetrahydrofuran.

It is also preferable to add an antioxidant such as 2,6-di-t-butyl-4-methylphenol to the recrystallization solvent in order to obtain a high-purity product. The antioxidant is used in an amount of 1 to 500 mg based on 100 g of the crystals of the target product.

The structure of the target product may be identified by measurement (e.g., NMR spectrum, IR spectrum, or mass spectrum), elementary analysis, or the like.

The compound (IV) used in connection with the embodiments of the invention may be produced as described below, for example.

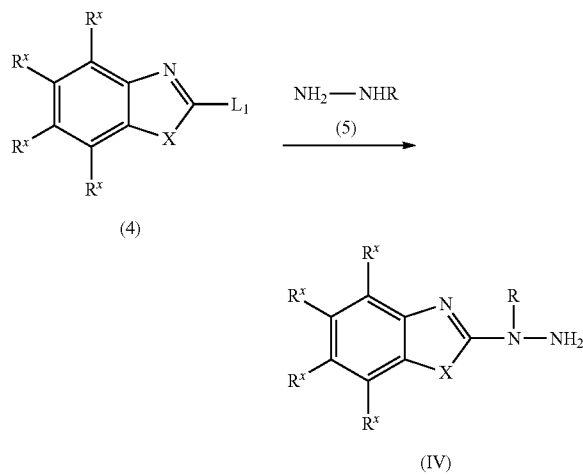

wherein $L^1$ represents a leaving group (e.g., halogen atom, methanesulfonyloxy group, or p-toluenesulfonyloxy group).

Specifically, the compound represented by the formula (4) (compound (4)) is reacted with the hydrazine compound (5) in an appropriate solvent in a molar ratio (compound (4): hydrazine compound (5)) of 1:1 to 1:20 (preferably 1:2 to 1:10) to obtain the compound (IV).

The solvent used for this reaction is not particularly limited as long as the solvent is inert to the reaction. Examples of the solvent include an alcohol such as methanol, ethanol, and n-propyl alcohol; an ether such as diethyl ether, tetrahydrofuran, 1,2-dimethoxyethane, 1,4-dioxane, and cyclopentyl methyl ether; an aromatic hydrocarbon such as benzene, toluene, and xylene; an aliphatic hydrocarbon such as n-pentane and n-hexane; an amide such as N,N-dimethylformamide; a sulfur-containing solvent such as dimethyl sulfoxide; a mixed solvent including two or more solvents among these solvents; and the like.

Among these, an alcohol, an ether, and a mixed solvent including an alcohol and an ether are preferable.

The reaction proceeds smoothly when the reaction temperature is set to a temperature within a range from −10° C. to the boiling point of the solvent. The reaction time is determined taking account of the reaction scale, but is normally set to several minutes to several hours.

The target product may be obtained by reacting the compound represented by the following formula (6) with a compound represented by the formula (7): R-Hal in an appropriate solvent in the presence of a base.

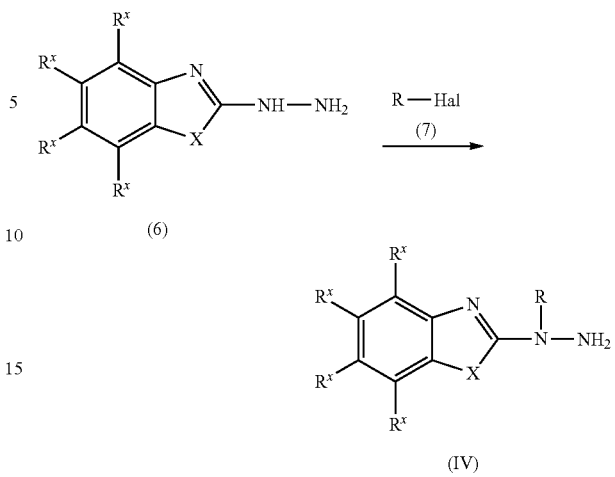

Examples of the base include an alkali metal carbonate such as potassium carbonate; an alkaline-earth metal carbonate such as calcium carbonate; an alkali metal hydroxide such as sodium hydroxide; an alkaline-earth metal hydroxide such as calcium hydroxide; and the like.

The base is normally used in a ratio of 1 to 8 equivalents based on the compound (6).

The reaction is preferably effected in a solvent. The reaction is more preferably effected in an aprotic polar solvent.

Examples of the aprotic polar solvent include a ketone-based solvent such as acetone, methyl ethyl ketone, 2-pentanone, 2-hexanone, methyl isobutyl ketone, and diisobutyl ketone; an ester-based solvent such as methyl acetate, ethyl acetate, propyl acetate, isopropyl acetate, butyl acetate, methyl propionate, and ethyl propionate; a sulfone-based solvent such as diethyl sulfone and diphenyl sulfone; a sulfoxide-based solvent such as dimethyl sulfoxide; an amine-based solvent such as N,N,N',N'-tetramethylethylenediamine and N,N-dimethylaniline; an amide-based solvent such as N,N-dimethylformamide, N,N-dimethylacetamide, and N-methylpyrrolidone; a urea-based solvent such as 1,3-dimethyl-2-imidazolidinone; a nitrile-based solvent such as acetonitrile, propionitrile, and benzonitrile; a nitro compound such as nitromethane and nitrobenzene; and the like. These solvents may be used either alone or in combination.

The solvent may be used in an arbitrary amount. The solvent is normally used in an amount of 0.1 to 50 mL, preferably 0.5 to 20 mL, and more preferably 1 to 15 mL, per gram of the compound (6).

The compound (6) and the compound (7) are normally used in a molar ratio (compound (6):compound (7)) of 1:1 to 1:2, and preferably 1:1 to 1:1.3.

The reaction temperature is normally set to a temperature within a range from −10° C. to the boiling point of the solvent, and preferably 0 to 70° C. The reaction time is determined taking account of the reaction scale, but is normally set to several minutes to 20 hours.

Note that the reaction is preferably effected in an inert atmosphere (e.g., under a nitrogen stream).

According to the embodiments of the invention, it is possible to obtain a high-purity polymerizable compound that has a very low ionic impurity content. It is possible to form a high-quality liquid crystal layer without an alignment defect by utilizing the polymerizable compound obtained using the method according to the embodiments of the invention.

EXAMPLES

The invention is further described below by way of examples. Note that the invention is not limited to the following examples.

Example 1

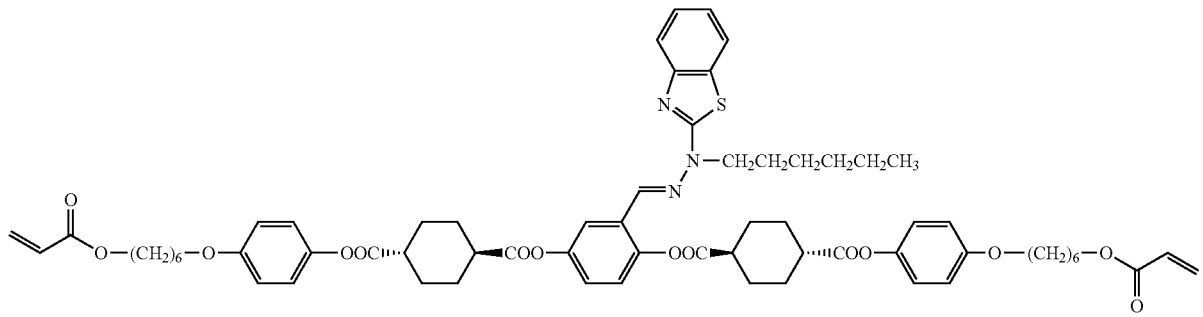

Compound 1

Step 1: Synthesis of Intermediate A

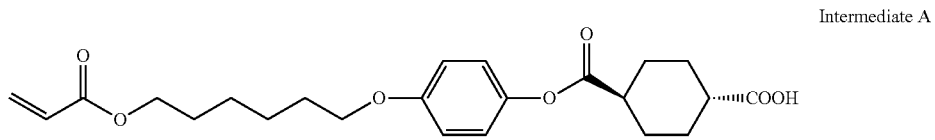 [SMILES: C=CC(=O)OCCCCCCOc1ccc(OC(=O)[C@H]2CC[C@H](C(=O)O)CC2)cc1]

Intermediate A

A three-necked reactor equipped with a thermometer was charged with 90 g (0.52 mol) of trans-1,4-cyclohexanedicarboxylic acid and 800 mL of tetrahydrofuran (THF) under a nitrogen stream. After the addition of 33 g (0.29 mol) of methanesulfonyl chloride to the mixture, the reactor was immersed in a water bath to adjust the temperature of the reaction mixture to 20° C. 31.7 g (0.31 mol) of triethylamine was added dropwise to the reaction mixture over 30 minutes while maintaining the temperature of the reaction mixture at 20 to 30° C. After the dropwise addition, the mixture was stirred at 25° C. for 2 hours.

After the addition of 3.2 g (26.2 mmol) of 4-(dimethylamino)pyridine and 69 g (0.26 mol) of 4-(6-acryloyloxyhex-1-yloxy)phenol (manufactured by DKSH) to the reaction mixture, the reactor was immersed in a water bath to adjust the temperature of the reaction mixture to 15° C. 31.7 g (0.31 mmol) of triethylamine was added dropwise to the reaction mixture over 30 minutes while maintaining the temperature of the reaction mixture at 20 to 30° C. After the dropwise addition, the mixture was stirred at 25° C. for 2 hours. After completion of the reaction, 4,000 mL of distilled water and 500 mL of a saturated sodium chloride solution were added to the reaction mixture, followed by extraction twice with 1,000 mL of ethyl acetate. The organic layer was collected, and dried over anhydrous sodium sulfate, and sodium sulfate was filtered off. The solvent was evaporated from the filtrate using a rotary evaporator, and the residue was purified by silica gel column chromatography (THF: toluene=1:9 (volume ratio (hereinafter the same)) to obtain 70.6 g of an intermediate A as a white solid (yield: 65%).

The structure of the target product was identified by $^1$H-NMR.

$^1$H-NMR (500 MHz, DMSO-$d_6$, TMS, δ ppm): 12.12 (s, 1H), 6.99 (d, 2H, J=9.0 Hz), 6.92 (d, 2H, J=9.0 Hz), 6.32 (dd, 1H, J=1.5 Hz, 17.5 Hz), 6.17 (dd, 1H, J=10.0 Hz, 17.5 Hz), 5.93 (dd, 1H, J=1.5 Hz, 10.0 Hz), 4.11 (t, 2H, J=6.5 Hz), 3.94 (t, 2H, J=6.5 Hz), 2.48-2.56 (m, 1H), 2.18-2.26 (m, 1H), 2.04-2.10 (m, 2H), 1.93-2.00 (m, 2H), 1.59-1.75 (m, 4H), 1.35-1.52 (m, 8H)

Step 2: Synthesis of Intermediate B

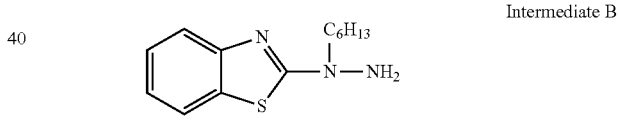

Intermediate B

A four-necked reactor equipped with a thermometer was charged with 20.0 g (0.12 mol) of 2-hydrazinobenzothiazole and 200 mL of N,N-dimethylformamide under a nitrogen stream to prepare a homogeneous solution. After the addition of 83.6 g (0.61 mol) of potassium carbonate and 30.8 g (0.15 mol) of 1-iodohexane to the solution, the mixture was stirred at 50° C. for 7 hours. After completion of the reaction, the reaction mixture was cooled to 20° C., and added to 1,000 mL of water, followed by extraction with 800 mL of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25) to obtain 21.0 g of an intermediate B as a white solid (yield: 69.6%).

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 8.0 Hz, 8.0 Hz), 7.06 (ddd, 1H, J=1.0 Hz, 8.0 Hz, 8.0 Hz), 4.22 (s, 2H), 3.74 (t, 2H, J=7.5 Hz), 1.69-1.76 (m, 2H), 1.29-1.42 (m, 6H), 0.89 (t, 3H, J=7.0 Hz)

Step 3: Synthesis of Intermediate C

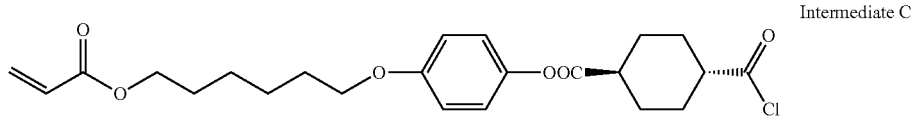

Intermediate C

A three-necked reactor equipped with a thermometer was charged with 30 g (71.7 mol) of the intermediate A synthesized by the step 1, 300 g of toluene, and 5.5 g of N,N-dimethylformamide under a nitrogen stream, and the mixture was cooled to 10° C. or less. 8.96 g (75.3 mmol) of thionyl chloride was added dropwise to the mixture while maintaining the reaction temperature at 10° C. or less. After the dropwise addition, the reaction mixture was returned to 25° C., and stirred for 1 hour. After completion of the reaction, the reaction mixture was concentrated using an evaporator until the amount of the reaction mixture was halved. After the addition of toluene in the same amount as the amount of the reaction mixture evaporated, the reaction mixture was concentrated using an evaporator until the amount of the reaction mixture was halved. The above operation was repeated three times to obtain a solution of an intermediate C in toluene.

Step 4: Synthesis of Compound 1

A three-necked reactor equipped with a thermometer was charged with 4.13 g (29.9 mmol) of 2,5-dihydroxybenzaldehyde, 7.62 g (75.4 mmol) of triethylamine, and 150 g of THF under a nitrogen stream to prepare a solution. The solution was cooled to 10° C. or less. The solution of the intermediate C in toluene (150 g) obtained by the step 3 was slowly added dropwise to the solution while maintaining the reaction temperature at 10° C. or less. After the dropwise addition, the mixture was stirred at 5 to 10° C. for 1 hour (step (1)). The reaction mixture became creamy due to the precipitation of triethylamine hydrochloride produced by the reaction.

After completion of the reaction, 9.7 g (38.9 mmol) of the intermediate B synthesized by the step 2 and 30 g of a 1.0 N hydrochloric acid aqueous solution were added to the reaction mixture while maintaining the reaction mixture at 10° C. or less. The reaction mixture was then heated to 40° C. to effect a reaction for 5 hours (step (2)). The triethylamine hydrochloride that had precipitated was dissolved when the reaction mixture was heated to 40° C., and a transparent two-layer solution including a toluene layer and an aqueous layer was obtained.

After completion of the reaction, the reaction mixture was cooled to 25° C., and 300 g of ethyl acetate and 300 g of a 10 wt % sodium chloride solution were added to the reaction mixture to effect separation. The resulting organic layer was washed twice with 300 g of a 2 wt % sodium chloride solution.

Step 5: Precipitation

About 15% (based on the total weight) of the organic layer was evaporated using an evaporator (i.e., the organic layer was concentrated). After cooling the solution to 25° C., a mixed solvent including 300 g of methanol and 60 g of water was slowly added dropwise to the solution. The mixture was cooled to 10° C. to precipitate crystals, which were filtered off.

Step 6: Recrystallization 240 g of THF, 240 g of methanol, and 20 mg of 2,6-di-t-butyl-4-methylphenol were added to the crystals, and the mixture was heated to 50° C. to obtain a homogeneous solution. The solution was subjected to hot filtration at 50° C., and the filtrate was slowly cooled to 10° C. to effect recrystallization. The resulting crystals were filtered off, and dried using a vacuum dryer to obtain 25.8 g of a compound 1 (yield: 73.7%).

The structure of the target product was identified by $^1$H-NMR.

$^1$H-NMR (400 MHz, CDCl$_3$, TMS, δ ppm): 7.75 (d, 1H, J=2.5 Hz), 7.67-7.70 (m, 3H), 7.34 (ddd, 1H, J=1.0 Hz, 7.0 Hz, 7.5 Hz), 7.17 (ddd, 1H, J=1.0 Hz, 7.5 Hz, 7.5 Hz), 7.12 (d, 1H, J=9.0 Hz), 7.10 (dd, 1H, J=2.5 Hz, 9.0 Hz), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.0 Hz), 6.13 (dd, 2H, J=10.5 Hz, 17.5 Hz), 5.82 (dd, 2H, J=1.5 Hz, 10.5 Hz), 4.30 (t, 2H, J=8.0 Hz), 4.18 (t, 4H, J=6.5 Hz), 3.95 (t, 4H, J=6.5 Hz), 2.58-2.70 (m, 4H), 2.31-2.35 (m, 8H), 1.66-1.82 (m, 18H), 1.31-1.54 (m, 14H), 0.90 (t, 3H, J=7.0 Hz)

Example 2

24.8 g of the compound 1 was obtained (yield: 70.9%) substantially in the same manner as in Example 1, except that 30 g of a 1.0 mol/L methanesulfonic acid aqueous solution was used in the step 4 instead of 30 g of a 1.0 N hydrochloric acid aqueous solution.

Example 3

25.0 g of the compound 1 was obtained (yield: 71.4%) substantially in the same manner as in Example 1, except that 30 g of a 1.0 mol/L camphorsulfonic acid aqueous solution was used in the step 4 instead of 30 g of a 1.0 N hydrochloric acid aqueous solution.

Example 4

The steps 1 to 5 were performed substantially in the same manner as in Example 3 to precipitate crystals, and the crystals were dried using a vacuum dryer (i.e., the step 6 (recrystallization) was not performed) to obtain 26.3 g of the compound 1 (yield: 75.1%).

Example 5

The steps 1 to 4 were performed substantially in the same manner as in Example 3, and the resulting organic layer was concentrated to precipitate a solid. 240 g of THF, 240 g of methanol, and 20 mg of 2,6-di-t-butyl-4-methylphenol were added to the solid, and the mixture was heated to 50° C. to obtain a homogeneous solution (substantially in the same manner as in the step 6 of Example 1). The solution was subjected to hot filtration at 50° C., and the filtrate was slowly cooled to 10° C. to effect recrystallization. The resulting crystals were filtered off, and dried using a vacuum dryer to obtain 25.1 g of the compound 1 (yield: 71.7%).

Example 6

The steps 1 and 2 were performed substantially in the same manner as in Example 1. In the step 3, a three-necked reactor equipped with a thermometer was charged with 30 g (71.7 mmol) of the intermediate A synthesized by the step 1, 300 g of chloroform, and 5.5 g of N,N-dimethylformamide under a nitrogen stream, and the mixture was cooled to 10° C. or less. 8.96 g (75.3 mmol) of thionyl chloride was added dropwise to the mixture while maintaining the reaction temperature at 10° C. or less. After the dropwise addition, the reaction mixture was heated to 25° C., and stirred for 1 hour. After completion of the reaction, the reaction mixture was concentrated using an evaporator until the amount of the reaction mixture was halved. After the addition of chloroform in the same amount as the amount of the reaction mixture evaporated, the reaction mixture was concentrated using an evaporator until the amount of the reaction mixture was halved. The above operation was repeated three times to obtain a solution of the intermediate C in chloroform.

In the step 4, a three-necked reactor equipped with a thermometer was charged with 4.13 g (29.9 mmol) of 2,5-dihydroxybenzaldehyde, 7.62 g (75.4 mmol) of triethylamine, and 150 g of chloroform under a nitrogen stream to prepare a solution. The solution was cooled to 10° C. or less. The solution of the intermediate C in chloroform (150 g) obtained by the step 3 was slowly added dropwise to the solution while maintaining the reaction temperature at 10° C. or less. After the dropwise addition, the mixture was stirred at 5 to 10° C. for 1 hour (step (1)). The reaction mixture became a transparent and homogeneous solution.

After completion of the reaction, 9.7 g (38.9 mmol) of the intermediate B synthesized by the step 2 and 30 g of a 1.0 N hydrochloric acid aqueous solution were added to the reaction mixture while maintaining the reaction mixture at 10° C. or less. The reaction mixture was then heated to 40° C. to effect a reaction for 3 hours (step (2)).

After completion of the reaction, the reaction mixture was cooled to 25° C., and a separation operation was performed. The resulting organic layer was subjected directly to the subsequent step without washing.

A precipitation operation and a recrystallization operation were performed substantially in the same manner as in the steps 5 and 6 of Example 1 to obtain 24.5 g of the compound 1 (yield: 70.0%).

Example 7

The steps 1 and 2 were performed substantially in the same manner as in Example 1. In the step 3, a three-necked reactor equipped with a thermometer was charged with 30 g (71.7 mmol) of the intermediate A synthesized by the step 1, 300 g of butyl acetate, and 5.5 g of N,N-dimethylformamide under a nitrogen stream, and the mixture was cooled to 10° C. or less. 8.96 g (75.3 mmol) of thionyl chloride was added dropwise to the mixture while maintaining the reaction temperature at 10° C. or less. After the dropwise addition, the reaction mixture was returned to 25° C., and stirred for 1 hour. After completion of the reaction, the reaction mixture was concentrated using an evaporator until the amount of the reaction mixture was halved. After the addition of butyl acetate substantially in the same amount as the amount of the reaction mixture evaporated, the reaction mixture was concentrated using an evaporator until the amount of the reaction mixture was halved. The above operation was repeated three times to obtain a solution of the intermediate C in butyl acetate.

In the step 4, a three-necked reactor equipped with a thermometer was charged with 4.13 g (29.9 mmol) of 2,5-dihydroxybenzaldehyde, 7.62 g (75.4 mmol) of triethylamine, and 150 g of butyl acetate under a nitrogen stream to prepare a solution. The solution was cooled to 10° C. or less. The solution of the intermediate C in butyl acetate (150 g) obtained by the step 3 was slowly added dropwise to the solution while maintaining the reaction temperature at 10° C. or less. After the dropwise addition, the mixture was stirred at 5 to 10° C. for 1 hour (step (1)). The reaction mixture became a transparent and homogeneous solution.

After completion of the reaction, 9.7 g (38.9 mmol) of the intermediate B synthesized by the step 2 and 30 g of a 1.0 N hydrochloric acid aqueous solution were added to the reaction mixture while maintaining the reaction mixture at 10° C. or less. The reaction mixture was then heated to 50° C. to effect a reaction for 3 hours (step (2)). The triethylamine hydrochloride that had precipitated was dissolved when the reaction mixture was heated to 50° C., and a transparent two-layer solution including a butyl acetate layer and an aqueous layer was obtained.

After completion of the reaction, the reaction mixture was cooled to 25° C., and a separation operation was performed. The resulting organic layer was subjected directly to the subsequent step without washing.

A precipitation operation and a recrystallization operation were performed in the same manner as in the steps 5 and 6 of Example 1 to obtain 24.3 g of the compound 1 (yield: 69.4%).

Example 8

The steps 1 and 2 were performed substantially in the same manner as in Example 1. In the step 3, a three-necked reactor equipped with a thermometer was charged with 30 g (71.7 mmol) of the intermediate A synthesized by the step 1, 300 g of cyclopentyl methyl ether (CPME), and 5.5 g of N,N-dimethylformamide under a nitrogen stream, and the mixture was cooled to 10° C. or less. 8.96 g (75.3 mmol) of thionyl chloride was added dropwise to the mixture while maintaining the reaction temperature at 10° C. or less. After the dropwise addition, the reaction mixture was returned to 25° C., and stirred for 1 hour. After completion of the reaction, the reaction mixture was concentrated using an evaporator until the amount of the reaction mixture was halved. After the addition of CPME in the same amount as the amount of the reaction mixture evaporated, the reaction mixture was concentrated using an evaporator until the amount of the reaction mixture was halved. The above operation was repeated three times to obtain a solution of the intermediate C in CPME.

In the step 4, a three-necked reactor equipped with a thermometer was charged with 4.13 g (29.9 mmol) of 2,5-dihydroxybenzaldehyde, 7.62 g (75.4 mmol) of triethylamine, and 150 g of THF under a nitrogen stream to prepare a solution. The solution was cooled to 10° C. or less. The solution of the intermediate C in CPME (150 g) obtained by the step 3 was slowly added dropwise to the solution while maintaining the reaction temperature at 10° C. or less. After the dropwise addition, the mixture was stirred at 5 to 10° C. for 1 hour (step (1)). The reaction mixture became creamy due to the precipitation of triethylamine hydrochloride produced by the reaction.

After completion of the reaction, 9.7 g (38.9 mmol) of the intermediate B synthesized by the step 2 and 30 g of a 1.0 N hydrochloric acid aqueous solution were added to the reaction mixture while maintaining the reaction mixture at 10° C. or less. The reaction mixture was then heated to 45° C. to effect a reaction for 4 hours (step (2)). The triethylamine hydrochloride that had precipitated was dissolved when the reaction mixture was heated to 45° C., and a transparent two-layer solution including a CPME layer and an aqueous layer was obtained.

After completion of the reaction, the reaction mixture was cooled to 25° C., and a separation operation was performed.

A precipitation operation and a recrystallization operation were performed substantially in the same manner as in the steps 5 and 6 of Example 1 to obtain 24.1 g of the compound 1 (yield: 68.9%).

Example 9

The steps 1 and 2 were performed substantially in the same manner as in Example 1. In the step 3, a three-necked reactor equipped with a thermometer was charged with 30 g (71.7 mmol) of the intermediate A synthesized by the step 1, 300 g of CPME, and 5.5 g of N,N-dimethylformamide under a nitrogen stream, and the mixture was cooled to 10° C. or less. 8.96 g (75.3 mmol) of thionyl chloride was added dropwise to the mixture while maintaining the reaction temperature at 10° C. or less. After the dropwise addition, the reaction mixture was returned to 25° C., and stirred for 1 hour. After completion of the reaction, the reaction mixture was concentrated using an evaporator until the amount of the reaction mixture was halved. After the addition of CPME in the same amount as the amount of the reaction mixture evaporated, the reaction mixture was concentrated using an evaporator until the amount of the reaction mixture was halved. The above operation was repeated three times to obtain a solution of the intermediate C in CPME.

In the step 4, a three-necked reactor equipped with a thermometer was charged with 4.13 g (29.9 mmol) of 2,5-dihydroxybenzaldehyde, 7.62 g (75.4 mmol) of triethylamine, and 150 g of chloroform under a nitrogen stream to prepare a solution. The solution was cooled to 10° C. or less. The solution of the intermediate C in CPME (150 g) obtained by the step 3 was slowly added dropwise to the solution while maintaining the reaction temperature at 10° C. or less. After the dropwise addition, the mixture was stirred at 5 to 10° C. for 1 hour (step (1)). The reaction mixture became a suspension due to the precipitation of triethylamine hydrochloride produced by the reaction.

After completion of the reaction, 9.7 g (38.9 mmol) of the intermediate B synthesized by the step 2 and 30 g of a 1.0 N hydrochloric acid aqueous solution were added to the reaction mixture while maintaining the reaction mixture at 10° C. or less. The reaction mixture was then heated to 40° C. to effect a reaction for 3 hours (step (2)). The triethylamine hydrochloride that had precipitated was dissolved when the reaction mixture was heated to 40° C., and a transparent two-layer solution including an organic layer (CPME-chloroform layer) and an aqueous layer was obtained.

After completion of the reaction, the reaction mixture was cooled to 25° C., and a separation operation was performed.

A precipitation operation and a recrystallization operation were performed substantially in the same manner as in the steps 5 and 6 of Example 1 to obtain 24.9 g of the compound 1 (yield: 71.2%).

Example 10

The steps 1 and 2 were performed substantially in the same manner as in Example 1. In the step 3, a three-necked reactor equipped with a thermometer was charged with 30 g (71.7 mmol) of the intermediate A synthesized by the step 1, 300 g of chloroform, and 10.5 g of N,N-dimethylformamide under a nitrogen stream, and the mixture was cooled to 10° C. or less. 8.96 g (75.3 mmol) of thionyl chloride was added dropwise to the mixture while maintaining the reaction temperature at 10° C. or less. After the dropwise addition, the reaction mixture was returned to 25° C., and stirred for 1 hour. After completion of the reaction, the reaction mixture was concentrated using an evaporator until the amount of the reaction mixture decreased to a quarter of the initial amount. 75 g of chloroform was then added to the reaction mixture to obtain a solution of the intermediate C in chloroform.

In the step 4, a three-necked reactor equipped with a thermometer was charged with 4.13 g (29.9 mmol) of 2,5-dihydroxybenzaldehyde, 18.1 g (179 mmol) of triethylamine, and 150 g of chloroform under a nitrogen stream to prepare a solution. The solution was cooled to 10° C. or less. The solution of the intermediate C in chloroform (150 g) obtained by the step 3 was slowly added dropwise to the solution while maintaining the reaction temperature at 10° C. or less. After the dropwise addition, the mixture was stirred at 5 to 10° C. for 1 hour (step (1)). The reaction mixture became a transparent and homogeneous solution.

After completion of the reaction, 9.7 g (38.9 mmol) of the intermediate B synthesized by the step 2 and 118 g of a 1.0 N hydrochloric acid aqueous solution were added to the reaction mixture while maintaining the reaction mixture at 10° C. or less. The reaction mixture was then heated to 40° C. to effect a reaction for 3 hours (step (2)).

After completion of the reaction, a separation operation was performed. The resulting organic layer was subjected directly to the subsequent step without washing.

After the addition of 1.5 g of a filter aid ("ROKAHELP #479" manufactured by Mitsui Mining and Smelting Co., Ltd.) to the organic layer, the mixture was stirred for 30 minutes, and the filter aid was filtered off. About 35% (based on the total weight) of the resulting reaction mixture was evaporated using an evaporator (i.e., the reaction mixture was concentrated). The reaction mixture was cooled to 25° C., and slowly added dropwise to 780 g of methanol. The mixture was stirred for 30 minutes to precipitate crystals, which were filtered off.

After the addition of 195 g of THF, 1.5 g of a filter aid ("ROKAHELP #479" manufactured by Mitsui Mining and Smelting Co., Ltd.), and 300 mg of 2,6-di-t-butyl-4-methylphenol to the crystals, the mixture was stirred for 30 minutes, and the filter aid was filtered off. The resulting solution was slowly added dropwise to 300 g of methanol. The mixture was stirred for 30 minutes to precipitate crystals, which were filtered off, and dried using a vacuum dryer to obtain 26.7 g of the compound 1 (yield: 76.3%).

Comparative Example 1

The steps 1 to 3 were performed substantially in the same manner as in Example 1. In the step 4, a three-necked reactor equipped with a thermometer was charged with 4.13 g (29.9 mmol) of 2,5-dihydroxybenzaldehyde, 7.62 g (75.4 mmol) of triethylamine, and 150 g of THF under a nitrogen stream to prepare a solution. The solution was cooled to 10° C. or less. The solution of the intermediate C in toluene was slowly added dropwise to the solution while maintaining the reaction temperature at 10° C. or less. After the dropwise addition, the reaction mixture was stirred at 10° C. or less for 1 hour. The reaction mixture became creamy due to the precipitation of triethylamine hydrochloride produced by the reaction. After completion of the reaction, 9.7 g (38.9 mmol) of the intermediate B synthesized by the step 2 was added to the reaction mixture while maintaining the reaction mixture at 10° C. or less, followed by the addition of 700 mg of camphorsulfonic acid (solid). The reaction mixture was then heated to 40° C. to effect a reaction for 5 hours. The triethylamine hydrochloride that had precipitated was not dissolved, and the reaction mixture remained creamy even when the reaction mixture was heated to 40° C. After completion of the reaction, the reaction mixture was cooled to 25° C., and 300 g of ethyl acetate and 300 g of a 10 wt % sodium chloride solution were added to the reaction mixture to effect separation. The resulting organic layer was washed twice with 300 g of a 2 wt % sodium chloride solution.

A precipitation operation and a recrystallization operation were performed substantially in the same manner as in the steps 5 and 6 of Example 1 to obtain 23.5 g of the compound 1 (yield: 67.1%).

Comparative Example 2

The steps 1 to 3 were performed substantially in the same manner as in Example 1. In the step 4, a three-necked reactor equipped with a thermometer was charged with 4.13 g (29.9 mmol) of 2,5-dihydroxybenzaldehyde, 7.62 g (75.4 mmol) of triethylamine, and 150 g of THF under a nitrogen stream to prepare a solution. The solution was cooled to 10° C. or less. The solution of the intermediate C in toluene was slowly added dropwise to the solution while maintaining the reaction temperature at 10° C. or less. After the dropwise addition, the reaction mixture was stirred at 10° C. or less for 1 hour. The reaction mixture became creamy due to the precipitation of triethylamine hydrochloride produced by the reaction. After completion of the reaction, 9.7 g (38.9 mmol) of the intermediate B was added to the reaction mixture while maintaining the reaction mixture at 10° C. or less, followed by the addition of 35 g of a 1.0 mol/L solution of camphorsulfonic acid in toluene. The reaction mixture was then heated to 40° C. to effect a reaction for 5 hours. The triethylamine hydrochloride that had precipitated was not dissolved, and the reaction mixture remained creamy even when the reaction mixture was heated to 40° C. After completion of the reaction, the reaction mixture was cooled to 25° C., and 300 g of ethyl acetate and 300 g of a 10 wt % sodium chloride solution were added to the reaction mixture to effect separation. The resulting organic layer was washed twice with 300 g of a 2 wt % sodium chloride solution.

A precipitation operation and a recrystallization operation were performed substantially in the same manner as in the steps 5 and 6 of Example 1 to obtain 24.8 g of the compound 1 (yield: 70.9%).

Comparative Example 3

The steps 1 to 3 were performed substantially in the same manner as in Example 1. In the step 4, a three-necked reactor equipped with a thermometer was charged with 4.13 g (29.9 mmol) of 2,5-dihydroxybenzaldehyde, 7.62 g (75.4 mmol) of triethylamine, and 150 g of THF under a nitrogen stream to prepare a solution. The solution was cooled to 10° C. or less. The solution of the intermediate C in toluene was slowly added dropwise to the solution while maintaining the reaction temperature at 10° C. or less. After the dropwise addition, the mixture was reacted at 10° C. or less for 1 hour. The reaction mixture became creamy due to the precipitation of triethylamine hydrochloride produced by the reaction. After completion of the reaction, 300 g of ethyl acetate and 500 g of a 10 wt % sodium chloride solution were added to the reaction mixture to effect separation. The resulting organic layer was washed twice with 500 g of a 2 wt % sodium chloride solution. The organic layer was cloudy since the separation was insufficient. The organic layer was concentrated using an evaporator. A solid obtained by the concentration was dissolved in 150 g of THF, and the solution was cooled to 10° C. or less. After the addition of 9.7 g (38.9 mmol) of the intermediate B to the solution, 30 g of a 1.0 N hydrochloric acid aqueous solution was added to the mixture. The reaction mixture was then heated to 40° C. to effect a reaction for 5 hours. The triethylamine hydrochloride that had precipitated was dissolved when the reaction mixture was heated to 40° C., and a transparent two-layer solution including a toluene layer and an aqueous layer was obtained. After completion of the reaction, the reaction mixture was cooled to 25° C., and 300 g of ethyl acetate and 300 g of a 10 wt % sodium chloride solution were added to the reaction mixture to effect separation.

A precipitation operation and a recrystallization operation were performed on the resulting organic layer substantially in the same manner as in the steps 5 and 6 of Example 1 to obtain 19.2 g of the compound 1 (yield: 54.9%).

Comparative Example 4

The steps 1 to 3 were performed substantially in the same manner as in Example 1. In the step 4, a three-necked reactor equipped with a thermometer was charged with 4.13 g (29.9 mmol) of 2,5-dihydroxybenzaldehyde, 7.62 g (75.4 mmol) of triethylamine, and 150 g of THF under a nitrogen stream to prepare a solution. The solution was cooled to 10° C. or less. The solution of the intermediate C in toluene was slowly added dropwise to the solution while maintaining the reaction temperature at 10° C. or less. After the dropwise addition, the mixture was reacted at 10° C. or less for 1 hour. The reaction mixture became creamy due to the precipitation of triethylamine hydrochloride produced by the reaction. After completion of the reaction, 300 g of ethyl acetate and 500 g of a 10 wt % sodium chloride solution were added to the reaction mixture to effect separation. The resulting organic layer was washed twice with 500 g of a 2 wt % sodium chloride solution. The organic layer was cloudy since the separation was insufficient. The organic layer was concentrated using an evaporator while maintaining the organic layer at 10° C. or less. A solid obtained by the concentration was dissolved in 150 g of THF, and the solution was cooled to 10° C. or less. After the addition of 9.7 g (38.9 mmol) of the intermediate B to the solution, 35 g of a 1.0 mol/L solution of camphorsulfonic acid in toluene was added to the mixture. The reaction mixture was then heated to 40° C. to effect a reaction for 5 hours. The triethylamine hydrochloride that had precipitated was not dissolved, and the reaction mixture remained creamy even when the reaction mixture was heated to 40° C. After completion of the reaction, the reaction mixture was cooled to 25° C., and 300 g of ethyl acetate and 300 g of a 10 wt % sodium chloride solution were added to the reaction mixture to effect separation. The resulting organic layer was washed twice with 300 g of a 2 wt % sodium chloride solution.

A precipitation operation and a recrystallization operation were performed on the resulting organic layer substantially in the same manner as in the steps 5 and 6 of Example 1 to obtain 18.2 g of the compound 1 (yield: 52.0%).

The following tests were performed using the compounds 1 obtained in Examples 1 to 10 and Comparative Examples 1 to 4.
I. Analysis of Ion Content
I-1 Preparation of Sample (Analysis Sample)

0.5 g of the compound 1 (compounds 1 obtained in Examples 1 to 10 and Comparative Examples 1 to 4) was dissolved in 10 g of chloroform in a 50 mL sample tube that had been washed and was free from ionic impurities. After the addition of 15 g of ultrapure water to the solution, the mixture was vigorously shaken for 5 minutes using a shaker. After allowing the mixture to stand for 30 minutes to effect oil-water separation, only the aqueous layer was filtered through a disc filter having a pore size of 0.45 µm to prepare an ion chromatography measurement sample.
I-2 Measurement of Ion Content The chlorine ion content in each sample was measured using an ion chromatograph ("DX-500" manufactured by Dionex). The results are shown in Table 1.
II. Evaluation of Alignment Properties
II-1 Preparation of Polymerizable Compositions 1 to 14

1.0 g of the compound 1 (compounds 1 obtained in Examples 1 to 10 and Comparative Examples 1 to 4), 30 mg of a photoinitiator ("Adekaoptomer N-1919" manufactured by Adeka Corporation), and 100 mg of a surfactant (1% cyclopentanone solution of KH-40 (manufactured by AGC Seimi Chemical Co., Ltd.)) were dissolved in 2.3 g of cyclopentanone. The solution was filtered through a disposable filter having a pore size of 0.45 µm to obtain a polymerizable composition (polymerizable compositions 1 to 14).
II-2 Evaluation of Alignment Properties The polymerizable composition (polymerizable compositions 1 to 14) was applied to a transparent glass substrate (provided with a polyimide alignment film subjected to a rubbing treatment) (manufactured by E.H.C. Co., Ltd.) using a #4 wire bar. After drying the resulting film at 110° C. for 1 minute, the film was subjected to an alignment treatment at 110° C. for 1 minute to form a liquid crystal layer to prepare an alignment property evaluation sample. The presence or absence of an alignment defect was observed at room temperature (25° C.) using a polarizing microscope ("ECLIPSE LV100 POL" manufactured by Nikon Corporation). A case where no alignment defect was observed was rated as "5", and a case where a number of alignment defects were observed was rated as "1". The number of alignment defects (amount of alignment defect) was evaluated in accordance with this standard. The evaluation results are shown in Table 1.

With regard to the item "Purification method" in Table 1, "Precipitation" means that an operation in accordance with the step 5 of Example 1 was performed, "Recrystallization" means that an operation in accordance with the step 6 of Example 1 was performed, and "Precipitation+recrystallization" means that the "Recrystallization" operation was performed after the "Precipitation" operation.

The invention claimed is:
1. A method for producing a polymerizable compound represented by a formula (I) comprising:
   a step (1) that reacts a compound represented by a formula (II) with 2,5-dihydroxybenzaldehyde in an organic solvent in the presence of a base to obtain a reaction mixture including a compound represented by a formula (III); and
   a step (2) that adds a compound represented by a formula (IV) and an acidic aqueous solution to the reaction mixture obtained by the step (1) to effect a reaction,

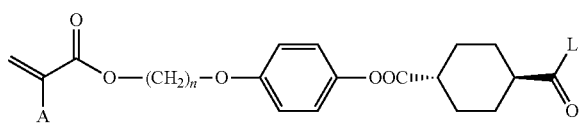

(II)

TABLE 1

| | Separation operation after esterification reaction | Reaction solvent | Acid | Purification method | Yield (%) | Chlorine ion content (ppm) | Polymerizable composition | Alignment properties |
|---|---|---|---|---|---|---|---|---|
| Example 4 | Not performed | Toluene + THF | Camphorsulfonic acid aqueous solution | Precipitation | 75.1 | 6.3 | 4 | 5 |
| Example 5 | Not performed | Toluene + THF | Camphorsulfonic acid aqueous solution | Recrystallization | 71.7 | 6.4 | 5 | 5 |
| Example 6 | Not performed | Chloroform | Hydrochloric acid aqueous solution | Precipitation + recrystallization | 70.0 | 5.1 | 6 | 5 |
| Example 7 | Not performed | Butyl acetate | Hydrochloric acid aqueous solution | Precipitation + recrystallization | 69.4 | 5.6 | 7 | 5 |
| Example 8 | Not performed | CPME + THF | Hydrochloric acid aqueous solution | Precipitation + recrystallization | 68.9 | 5.5 | 8 | 5 |
| Example 9 | Not performed | CPME + chloroform | Hydrochloric acid aqueous solution | Precipitation + recrystallization | 71.2 | 5.5 | 9 | 5 |
| Example 10 | Not performed | Chloroform | Hydrochloric acid aqueous solution | Precipitation + precipitation | 76.3 | 3.0 | 10 | 5 |
| Comparative Example 1 | Not performed | Toluene + THF | Camphorsulfonic acid (solid) | Precipitation + recrystallization | 67.1 | 186 | 11 | 2 |
| Comparative Example 2 | Not performed | Toluene + THF | Solution of camphorsulfonic acid in toluene | Precipitation + recrystallization | 70.9 | 103 | 12 | 3 |
| Comparative Example 3 | Performed | Toluene + THF | Camphorsulfonic acid aqueous solution | Precipitation + recrystallization | 54.9 | 7.2 | 13 | 5 |
| Comparative Example 4 | Performed | Toluene + THF | Solution of camphorsulfonic acid in toluene | Precipitation + recrystallization | 52.0 | 68 | 14 | 3 |

As is clear from the results shown in Table 1, a high-purity compound 1 was obtained in Examples 1 to 10 in high yield, and the polymerizable compositions 1 to 10 prepared using the compounds 1 obtained in Examples 1 to 10 exhibited excellent alignment properties.

On the other hand, when a solid acid was used in the step 4 instead of the acidic aqueous solution (Comparative Example 1), a low-purity compound 1 having a high chlorine ion content was obtained in low yield, and the polymerizable composition 11 obtained using the compound 1 obtained in Comparative Example 1 exhibited poor alignment properties. When a solution of an acid in toluene was used (Comparative Example 2), a low-purity compound 1 was obtained, and the polymerizable composition 12 obtained using the compound 1 obtained in Comparative Example 2 exhibited poor alignment properties. The yield of the compound 1 was low when the reaction mixture obtained by the step (1) was subjected to the step (2) through the separation operation (Comparative Examples 3 and 4).

wherein A represents a hydrogen atom, a methyl group, or a chlorine atom, L represents a a halogen atom or an organic sulfonyloxy group, and n represents an integer from 1 to 20,

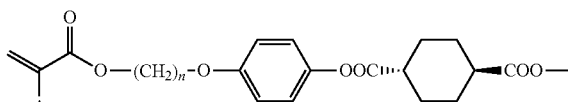

(III)

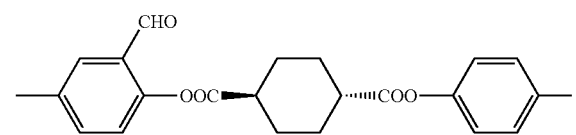

-continued

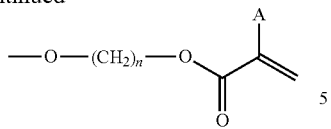

wherein A and n are the same as defined above,

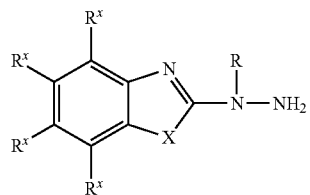

wherein X represents an oxygen atom, a sulfur atom, $-C(R^1)(R^2)-$, or $-N-R^1-$,
wherein each of $R^1$ and $R^2$ independently represents a hydrogen atom, or a substituted or unsubstituted alkyl group having 1 to 10 carbon atoms,
R represents a hydrogen atom, or a substituted or unsubstituted organic group having 1 to 20 carbon atoms, and
each of $R^x$ represents a hydrogen atom, a halogen atom, an alkyl group having 1 to 6 carbon atoms, a cyano group, a nitro group, a fluoroalkyl group having 1 to 6 carbon atoms, an alkoxy group having 1 to 6 carbon atoms, an alkylthio group having 1 to 6 carbon atoms, a monosubstituted amino group, a disubstituted amino group, or $-C(=O)-O-R^3$, wherein $R^3$ is the same as defined above in connection with $R^1$ and $R^2$, provided that $R^x$ are identical to or different from each other, and an arbitrary $C-R^x$ that forms the ring is optionally substituted with a nitrogen atom, and

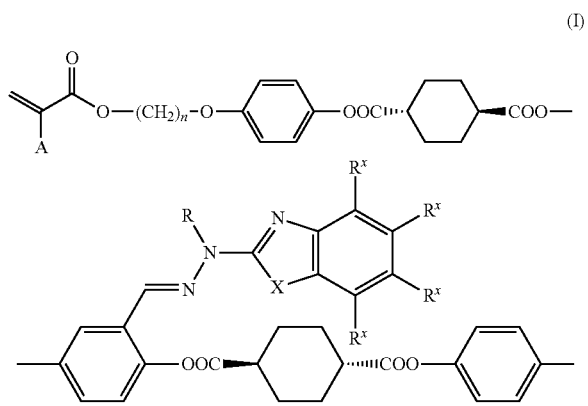

wherein A, R, $R^x$, X, and n are the same as defined above.

2. The method according to claim 1, wherein R included in the compound represented by the formula (IV) is a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted aromatic group having 6 to 18 carbon atoms, or a substituted or unsubstituted heteroaromatic group having 4 to 18 carbon atoms.

3. The method according to claim 1, wherein each of $R^x$ included in the compound represented by the formula (IV) is a hydrogen atom.

4. The method according to claim 1, wherein an acid component included in the acidic aqueous solution is an inorganic acid or an organic acid having 1 to 20 carbon atoms.

5. The method according to claim 1, wherein an acid component included in the acidic aqueous solution is at least one acid selected from a group consisting of hydrochloric acid, sulfuric acid, phosphoric acid, boric acid, a sulfonic acid, a sulfinic acid, formic acid, acetic acid, and oxalic acid.

6. A compound represented by a formula (II), wherein A represents a hydrogen atom, a methyl group, or a chlorine atom, L represents a halogen atom or an organic sulfonyloxy group, and n represents an integer from 1 to 20.

* * * * *